Oct. 27, 1970 R. M. MILFELD Plant Pat. 2,994
AZALEA PLANT
Filed July 29, 1968
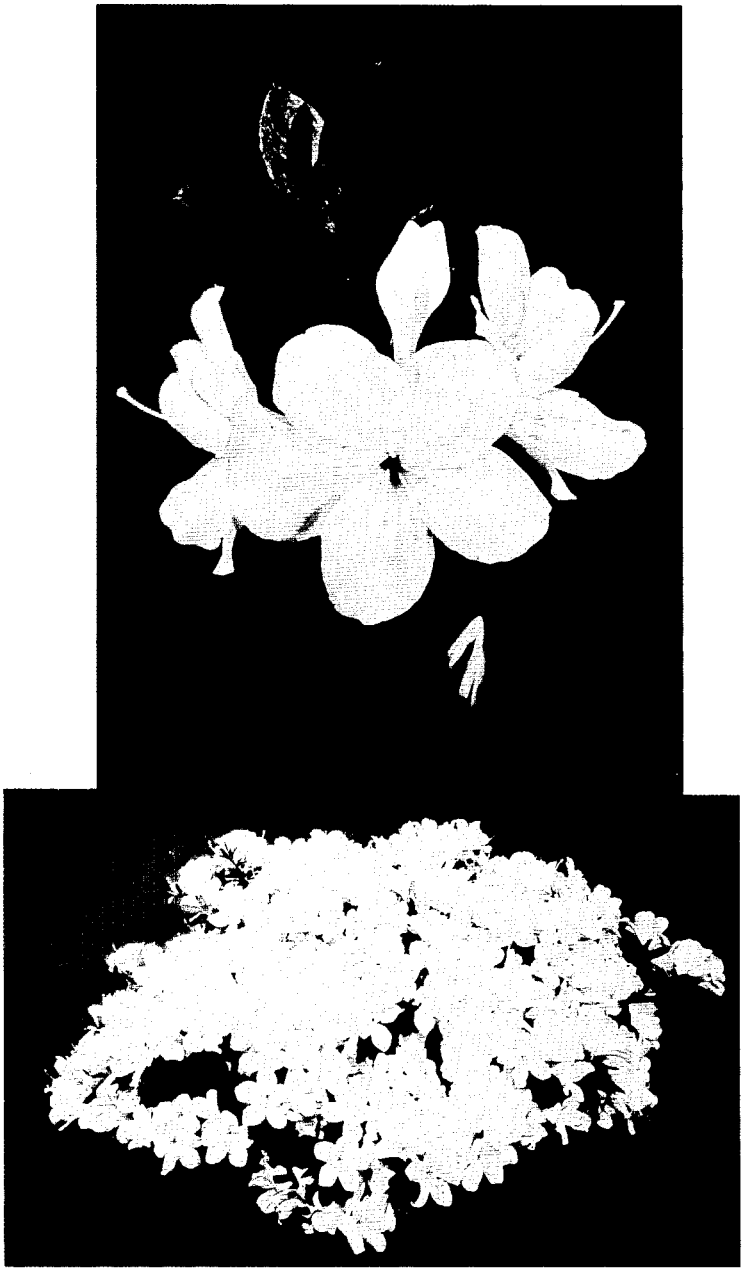
Inventor.
Raymond M. Milfeld
By: Robb & Robb
attorneys.

United States Patent Office

Plant Pat. 2,994
Patented Oct. 27, 1970

2,994
AZALEA PLANT

Raymond M. Milfeld, Monrovia, Calif., assignor to Milfelds' Nursery, Inc., Monrovia, Calif., a corporation of California

Filed July 29, 1968, Ser. No. 748,571
Int. Cl. A01h *5/00*
U.S. Cl. Plt.—55 1 Claim

The present invention relates to a new and distinct variety of azalea plant of the Indian azalea type, which was discovered by me as a sport of the azalea variety known as "Pink Lace" (Plant Pat. No. 2,757).

At the time of my discovery aforesaid, a large block of plants of the variety "Pink Lace" were being grown commercially under my direction and control in the nursery fields of my assignee, located at Monrovia, Calif. While tending these plants, my attention was attracted to one particular plant on which there was one branch which was bearing white flowers instead of the normal pink flowers of "Pink Lace." Upon close examination of this particular plant, I found that it had sported, and I thereupon took immediate steps to preserve the sport, keep it under close observation, and to asexually reproduce the same, as performed by propagating cuttings taken by me therefrom and planted in the nursery aforesaid. Continued observations and tests of the sport and the progeny thereof derived from the aforementioned cuttings have convinced me that my new sport comes true and is a new and distinct variety which is distinguished from its parent, as well as from all other azalea varieties of which I am aware, as evidenced by the following unique combination of characteristics which are outstanding therein:

(1) A low growing but more compact habit than the parent variety;

(2) A better, earlier and more massive blooming habit than the parent variety and other southern Indica types;

(3) Good disease resistance and hardiness comparable to the variety "Pink Lace";

(4) Attractive dark green foliage which is less yellow than most other white-flowered azaleas; and (5) A distinctive and attractive white flower color which presents a pleasing contrast with the dark green foliage.

The accompanying drawing shows a typical specimen plant of my new azalea variety, as well as typical specimen blooms thereof on an enlarged scale and in different stages of development, all as depicted in color as nearly true as it is reasonably possible to make the same in a color illustration of this character.

The following is a detailed description of the new variety, with color terminology in accordance with Wilson's Colour Chart published by the British Colour Council in collaboration with the Royal Horticultural Society, except where general color terms of ordinary dictionary significance are obvious:

Locality where grown and observed: San Gabriel Valley, Calif.

Parentage: Sport of "Pink Lace."

Propagation: Holds its distinguishing characteristics through succeeding propagations by cuttings.

Plant:

*Form.*—Bush; much branched; low growing (comparable to "Pink Lace" and "Duc De Rohan"—about 30 inches tall in 5 years, with normal pruning); compact.

*Habit.*—Vigorous; branching.

*Rooting.*—Roots easily.

*Foliage.*—Size—medium. Quantity—abundant. Color—new foliage: upper side—Spinach green, Plate 0960/2; under side—Spinach green, Plate 0960/1; old foliage: upper side—Spinach green, Plate 0960; under side—Spinach Green, Plate 0960/2. Shape—oval pointed. Texture—upper side—glossy; corrugated; under side—rough. Margin—entire; even edge, with light hairs. Aspect—oval pointed; center vein runs entire length and has lateral veins extended therefrom. Disease resistance—no evidence of any diseases to which azalea varieties are normally susceptible, as determined by comparison with other varieties grown under comparable conditions at Monrovia, Calif.

Flower:

*Blooming habit.*—Very prolific; massive.

*Blooming season.*—February through April; suitable for forcing.

*Borne.*—3 or 4 to stem; in regular clusters; on short stems.

*Quantity of blooms.*—Abundant, both outdoors and in greenhouse.

*Continuity.*—One season; in Spring of the year.

*Petalage.*—Number of petals under normal conditions—5. Size—from 2¼ inches to 2½ inches across "wing" petals. Color—white. Texture—inside: velvety; outside: smooth. Appearance—inside: white, with pale green on throat of from 1 to 3 petals; outside: white, with pale green on some petals that have green on inside; green color fades as flower ages. Shape—trumpet. Arrangement—3 petals at top and 2 petals at bottom.

Bud: Long tapered.

*Color.*—White.

Reproductive organs:

*Stamens.*—Color—pale green, with a central long one pale green at bottom. 8 or 9 small stamens.

*Pollen.*—Color—light amber.

*Styles.*—One long style in center measuring from 1¼ inches to 1½ inches in length.

*Ovaries.*—5 apple green carpels forming a grayish green seed pod.

General Observations: The new variety is similar to its parent "Pink Lace," in respect to its hardiness, foliage color and good disease resistance, but primarily differs therefrom by the attractive white color of its flowers, a better, earlier and more massive blooming habit, and a more compact plant form.

I claim:

1. A new and distinct variety of azalea plant of the Indian type, substantially as herein shown and described, characterized particularly as to novelty by the unique combination of a low growing but more compact habit than the parent variety, a better, earlier and more massive blooming habit than the parent variety and other southern Indica types, good disease resistance and hardiness comparable to the variety "Pink Lace," attractive dark green foliage which is less yellow than most other white-flowered azaleas, and a distinctive and attractive white flower color which presents a pleasing contrast with the dark green foliage.

No references cited.

ROBERT E. BAGWILL, Primary Examiner